United States Patent
Chang et al.

(10) Patent No.: US 11,123,564 B2
(45) Date of Patent: Sep. 21, 2021

(54) ELECTRICAL STIMULATION CONTROLLING DEVICE AND ELECTRICAL STIMULATION SYSTEM

(71) Applicant: A-Neuron Electronic Corporation, Hsinchu County (TW)

(72) Inventors: Chia-Chi Chang, Taipei (TW); Pei-Chen Lin, Hsinchu (TW); Cheng-Hsiang Cheng, New Taipei (TW)

(73) Assignee: A-Neuron Electronic Corporation, Hsinchu County (TW)

( * ) Notice: Subject to any disclaimer, the term of this patent is extended or adjusted under 35 U.S.C. 154(b) by 64 days.

(21) Appl. No.: 16/425,959

(22) Filed: May 30, 2019

(65) Prior Publication Data

US 2020/0376277 A1 Dec. 3, 2020

(51) Int. Cl.
*A61N 1/36* (2006.01)
*A61B 5/04* (2006.01)
(Continued)

(52) U.S. Cl.
CPC ............ *A61N 1/36139* (2013.01); *A61B 5/24* (2021.01); *A61B 5/7275* (2013.01); *A61N 1/36082* (2013.01)

(58) Field of Classification Search
CPC ............ A61N 1/36082; A61N 1/36139; A61N 1/36025; A61N 1/36031; A61N 1/3606;
(Continued)

(56) References Cited

U.S. PATENT DOCUMENTS 6,480,743 B1 11/2002 Kirkpatrick et al.
6,594,524 B2 7/2003 Esteller et al.
(Continued)

FOREIGN PATENT DOCUMENTS

| GN | 105956623 | 9/2016 |
| TW | I537022 | 6/2016 |

(Continued)

OTHER PUBLICATIONS

Alexandros T. Izallas et al., "Automated Epileptic Seizure Detection Methods: A Review Study," Epilepsy—Histological, Electroencephalographic and Psychological Aspects, Feb. 2012, pp. 75-98.
(Continued)

*Primary Examiner* — Carl H Layno
*Assistant Examiner* — Jane C Kalinock
(74) *Attorney, Agent, or Firm* — JCIP Global Inc.

(57) ABSTRACT

An electrical stimulation controlling device and an electrical stimulation system are provided. In which, the electrical stimulation controlling device includes a receiving circuit and a controller coupled to the receiving circuit. The receiving circuit is configured to receive an ictal neural signal which is a signal obtained by a detector when a neural event has been occurring. The controller is further coupled to a stimulator and configured to: determine a time point to start an electrical stimulation according to the ictal neural signal after an onset of the neural event has been determined; and generate and transmit a control signal to the stimulator for providing the electrical stimulation according to the determined time point.

14 Claims, 4 Drawing Sheets

(51) Int. Cl.
*A61B 5/00* (2006.01)
*A61B 5/24* (2021.01)

(58) Field of Classification Search
CPC ............ A61N 1/36064; A61N 1/36125; A61N 1/36146; A61B 5/04001; A61B 5/7275; A61B 5/24; A61B 5/369; A61B 5/4094; A61B 5/7282; G16H 20/30; G16H 50/20
USPC .......................................................... 607/45
See application file for complete search history.

(56) References Cited

U.S. PATENT DOCUMENTS

| | | | |
|---|---|---|---|
| 6,810,285 B2* | 10/2004 | Pless | A61B 5/7264 600/544 |
| 10,463,270 B2* | 11/2019 | Leyde | A61B 5/7264 |
| 10,506,988 B2* | 12/2019 | Karoly | A61B 5/24 |
| 2010/0168603 A1 | 7/2010 | Himes et al. | |
| 2011/0270357 A1 | 11/2011 | Torgerson et al. | |
| 2012/0271372 A1 | 10/2012 | Osorio | |
| 2012/0310050 A1 | 12/2012 | Osorio | |
| 2013/0253363 A1 | 9/2013 | Juffali et al. | |
| 2016/0228705 A1* | 8/2016 | Crowder | A61N 1/36139 |
| 2016/0367814 A1 | 12/2016 | Pless et al. | |

FOREIGN PATENT DOCUMENTS

| | | |
|---|---|---|
| TW | 201637679 | 11/2016 |
| TW | M567613 | 10/2018 |
| WO | 9726823 | 7/1997 |
| WO | 2007024702 | 3/2007 |
| WO | 2018005981 | 1/2018 |

OTHER PUBLICATIONS

Yu-Lin Wang et al., "An energy efficient real-time seizure detection method in rats with spontaneous temporal lobe epilepsy," 2013 IEEE Symposium on Computational Intelligence, Cognitive Algorithms, Mind, and Brain (CCMB), Apr. 16-19, 2013, pp. 29-35.
Wei-Ming Chen et al., "A Fully Integrated 8-Channel Closed-Loop Neural-Prosthetic CMOS SoC for Real-Time Epileptic Seizure Control," IEEE Journal of Solid-State Circuits, vol. 49, Issue 1, Jan. 2014, pp. 232-247.
Sriram Ramgopal et al., "Seizure detection, seizure prediction, and closed-loop warning systems in epilepsy," Epilepsy & Behavior, vol. 37, Aug. 2014, pp. 291-307.
Anjum Shaikh et al., "Critical Review of Epileptic Prediction Model Using EEG," International Journal of Modern Trends in Engineering and Research (IJMTER), vol. 3, Issue 4, Apr. 2016, pp. 182-191.
Sean R Mathieson et al., "Validation of an automated seizure detection algorithm for term neonates," Clinical Neurophysiology, vol. 127, Issue 1, Jan. 2016, pp. 156-168.
Su Liu et al., "High-frequency oscillations detected in ECoG recordings correlate with cavernous malformation and seizure-free outcome in a child with focal epilepsy: A case report," Epilepsia Open, vol. 2, Issue 2, Jun. 2017, pp. 262-272.
Kaushik Kumar Majumdar et al., "Automatic Seizure Detection in ECoG by Differential Operator and Windowed Variance," IEEE Transactions on Neural Systems and Rehabilitation Engineering, vol. 19, Issue 4, Aug. 2011, pp. 356-365.
Ivan Osorio et al., "Performance Reassessment of a Real-time Seizure-detection Algorithm on Long ECoG Series," Epilepsia, vol. 43, Issue 12, Dec. 2002, pp. 1522-1535.
Susana Blanco et al., "Comparison of Frequency Bands Using Spectral Entropy for Epileptic Seizure Prediction," ISRN Neurology, vol. 2013, May 8, 2013, pp. 1-5.
Lina Wang et al., "Automatic Epileptic Seizure Detection in EEG Signals Using Multi-Domain Feature Extraction and Nonlinear Analysis," Entropy, vol. 19, Issue 6, May 2017, pp. 1-17.
Edmund F. Hodkin et al., "Automated FES for Upper Limb Rehabilitation Following Stroke and Spinal Cord Injury," IEEE Transactions on Neural Systems and Rehabilitation Engineering, vol. 26, No. 5, May 2018, pp. 1067-1074.
Dejan B. Popović, "Control of Functional Electrical Stimulation for Restoration of Motor Function," Electronics and Energetics, vol. 30, Sep. 2017, pp. 295-312.
N. Fisekovic et al., "New controller for functional electrical stimulation systems," Medical Engineering & Physics, vol. 23, Issue 6, Jul. 2001, pp. 391-399.
"Search Report of Europe Counterpart Application", dated Mar. 31, 2020, p. 1-p. 8.
"Office Action of Taiwan Counterpart Application", dated Jan. 22, 2021, pp. 1-14.

* cited by examiner

ELECTRICAL STIMULATION CONTROLLING DEVICE AND ELECTRICAL STIMULATION SYSTEM

BACKGROUND

Technical Field

The invention relates to a neurological disease control, and more particularly, to an electrical stimulation controlling device and an electrical stimulation system.

Description of Related Art

Epilepsy is a common syndrome among chronic neurological diseases, and about 60 million people in the world suffer from epilepsy, while approximately 30% among them are still unable to effectively control the seizure by currently available antiepileptic drugs, and need non-pharmacological adjuvant therapies. Even though an epilepsy surgery may help, there are some patients who are not suitable for treatments of brain resection and are only allowed to select neuromodulation for mitigating severe seizures.

According to pathological and physiological characterization and characteristics of an electroencephalography (EEG) signal, several phases include inter-ictal, pre-ictal, irregular phase and burst phase can be defined. The last three belong to ictal phases of the seizure onset, and the conventional electrical stimulations are provided when the seizure onset is detected in the EEG signal. That is, the electrical stimulation starts from the pre-ictal phase. However, recent researches indicate that the stimulation is not equally effective when provided to every ictal phases. Prolonged electrical stimulation may increase the endurance of the patient thereto, therefore the effectiveness of the electrical stimulation to the patient may decrease gradually. And, it is power consuming as well.

SUMMARY

Accordingly, the embodiments of the invention provide an electrical stimulation controlling device and an electrical stimulation system capable of providing a proper electrical stimulation at a proper timing.

According to an embodiment of the invention, an electrical stimulation controlling device is provided. The electrical stimulation controlling device includes a receiving circuit and a controller coupled to the receiving circuit. The receiving circuit is configured to receive an ictal neural signal which is a signal obtained by a detector when a neural event has been occurring. The controller is further coupled to a stimulator and configured to: determine a time point to start an electrical stimulation according to the ictal neural signal after an onset of the neural event has been determined; and generate and transmit a control signal to the stimulator for providing the electrical stimulation according to the determined time point.

According to an embodiment of the invention, an electrical stimulation system is provided. The electrical stimulation system includes an event determination device, an electrical stimulation controlling device and a stimulator. The event determination device is coupled to a detector and configured to: receive a neural signal from the detector; detect an onset of a neural event according to the neural signal; and generate and transmit an onset signal to the electrical stimulation controlling device in response to the onset of the neural event detected. The electrical stimulation controlling device is coupled to the detector and the event determination device and configured to: receive the onset signal from the event determination device; acquire an ictal neural signal from the detector in response to the onset signal received; determine a time point to start an electrical stimulation according to the acquired ictal neural signal; and generate and transmit a control signal to the stimulator according to the determined time point. The stimulator is coupled to the electrical stimulation controlling device and configured to receive the control signal and provide the electrical stimulation according to the received control signal.

According to an embodiment of the invention, an electrical stimulation controlling device is provided. The electrical stimulation controlling device includes a receiving circuit and a controller coupled to the receiving circuit. The receiving circuit is configured to acquire an ictal neural signal which is a signal obtained by a detector when a neural event has been occurring. The controller is further coupled to a stimulator and configured to: identify a plurality of ictal phases in the ictal neural signal; generate a control signal according to the identified ictal phases; and transmit the control signal to the stimulator for providing an electrical stimulation.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
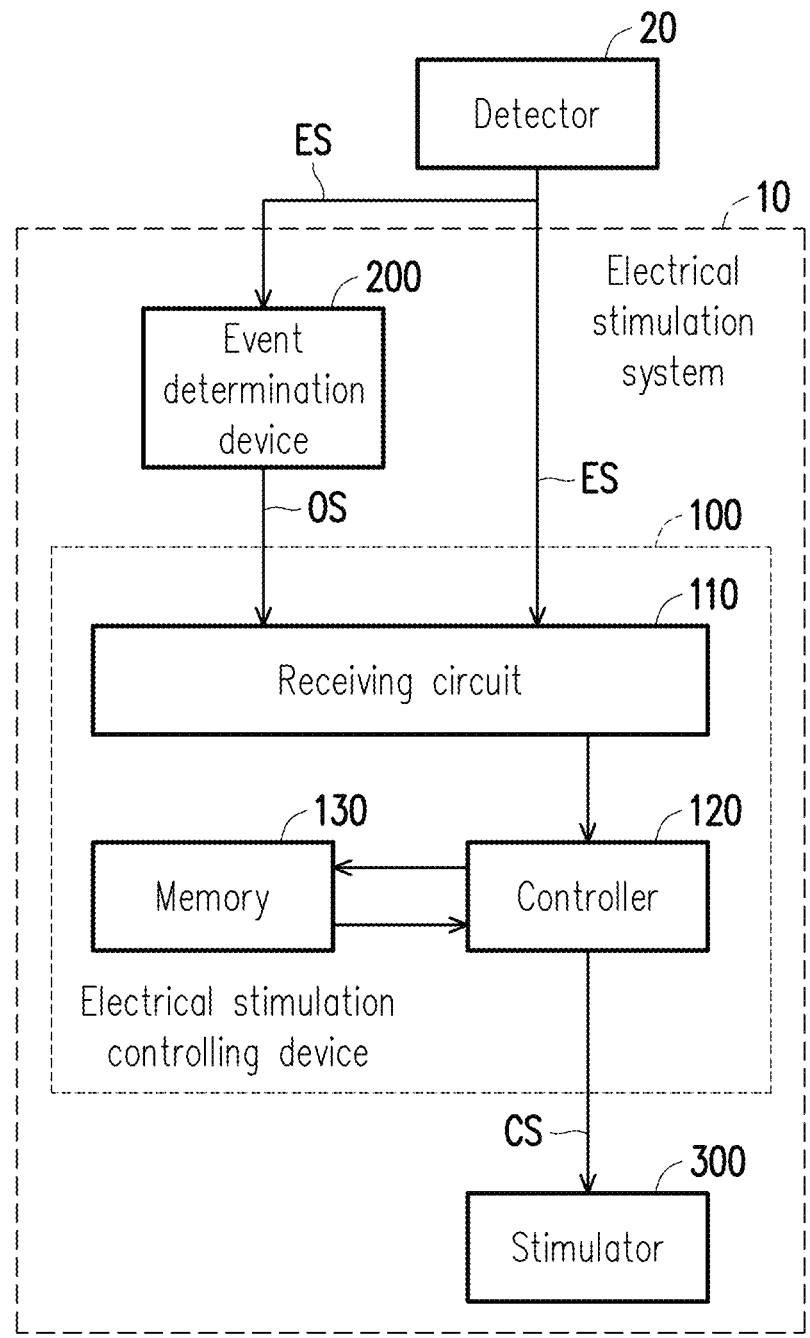
FIG. 1 illustrates a schematic block diagram of an electrical stimulation system according to an embodiment of the invention.

FIG. 1 illustrates a schematic block diagram of an electrical stimulation system according to an embodiment of the invention.

Referring to FIG. 1, an electrical stimulation system 10 includes an electrical stimulation controlling device 100, an event determination device 200 and a stimulator 300, wherein the event determination device 200 and the stimulator 300 are both coupled to the electrical stimulation controlling device 100. The electrical stimulation system 10 is configured to provide electrical stimulation for controlling an onset of a neural event of a subject (not shown). Noted that embodiments in the following description takes seizure an exemplary example of the neural event, but the invention is not limited thereto.

The detector 20 is configured to obtain a neural signal ES from the subject. The detector 20 may, for example, include electrodes of multiple (for example, 64) channels, which are respectively disposed at locations corresponding to different brainwave zones of the subject, thereby obtaining neural signals such as electroencephalography (EEG) signals of the subject. In the embodiment, the detector 20 may obtain the neural signal ES of the subject and transmit the same to the electronic stimulation system 10.

The electrical stimulation system 10 is configured to receive the neural signal ES of the subject from the detector 20, analysis the neural signal ES and provide a proper electrical stimulation to the subject at a proper timing. In the embodiment, the event determination device 200 is coupled to the detector 20 and configured to receive the neural signal ES from the detector 20, detect seizure onset in the neural signal, and generate and transmit an onset signal OS to the electrical stimulation controlling device 100 for telling it seizure onset was detected in the neural signal ES. The electrical stimulation controlling device 100 then acquires the neural signal ES from the detector 20 in response to the onset signal OS received, decides when and/or how to provide the electrical stimulation, and generates and provides a control signal CS to the stimulator 300 according to the decision made. The event determination device 200 is, for example, a device having a trained model such as an artificial neural network (ANN), support vector machine (SVM), a linear classification model, a fuzzy logic model or an auto-learn system, which is not limited herein. The stimulator 300 is, for example, a neurostimulator disposed at locations corresponding to different brainwave zones of the subject, configured to provide electrical stimulation to the subject according to the control signal CS, but which is not limited herein.

It is noted that the neural signal ES acquired by the electrical stimulation controlling device 100 in response to the onset signal OS received is also referred as to ictal neural signal ES hereinafter for clearly demonstrating that the seizure onset has been occurring therein. Essentially, the ictal neural signal ES is also a neural signal of the subject.

In some embodiments, after the electrical stimulation controlling device 100 is notified that the seizure onset has been occurring, it determines when to provide the electrical stimulation. Specifically, ictal phases of the seizure onset include pre-ictal, irregular phase and burst phase, the electrical stimulation controlling device 100 identifies multiple phases (e.g., at least the pre-ictal and the irregular phase) in the ictal neural signal ES and determines one of the ictal phase concerned (e.g., irregular phase) for providing the electrical stimulation.

More specifically, in some embodiments, the electrical stimulation controlling device 100 includes at least a receiving circuit 110 and a controller 120. The receiving circuit 110 is coupled to the event determination device 200 for receiving the onset signal OS and coupled to the detector 20 for receiving the ictal neural signal ES. The controller 120 is coupled to the receiving circuit 110 and the stimulator 300, which may be, a dual-core, quad-core, or octa-core central processing unit (CPU), a system-on-chip (SOC), an application processor, a media processor, a microprocessor, a digital signal processor, a programmable controller, application specific integrated circuits (ASIC), a programmable logic device (PLD) or other similar devices or a combination of these devices, which is not limited in the invention. Once the receiving circuit 110 receives the onset signal OS, the controller 120 determines the seizure onset accordingly and acquires the ictal neural signal ES through the receiving circuit 110.

Figures 2, 3:
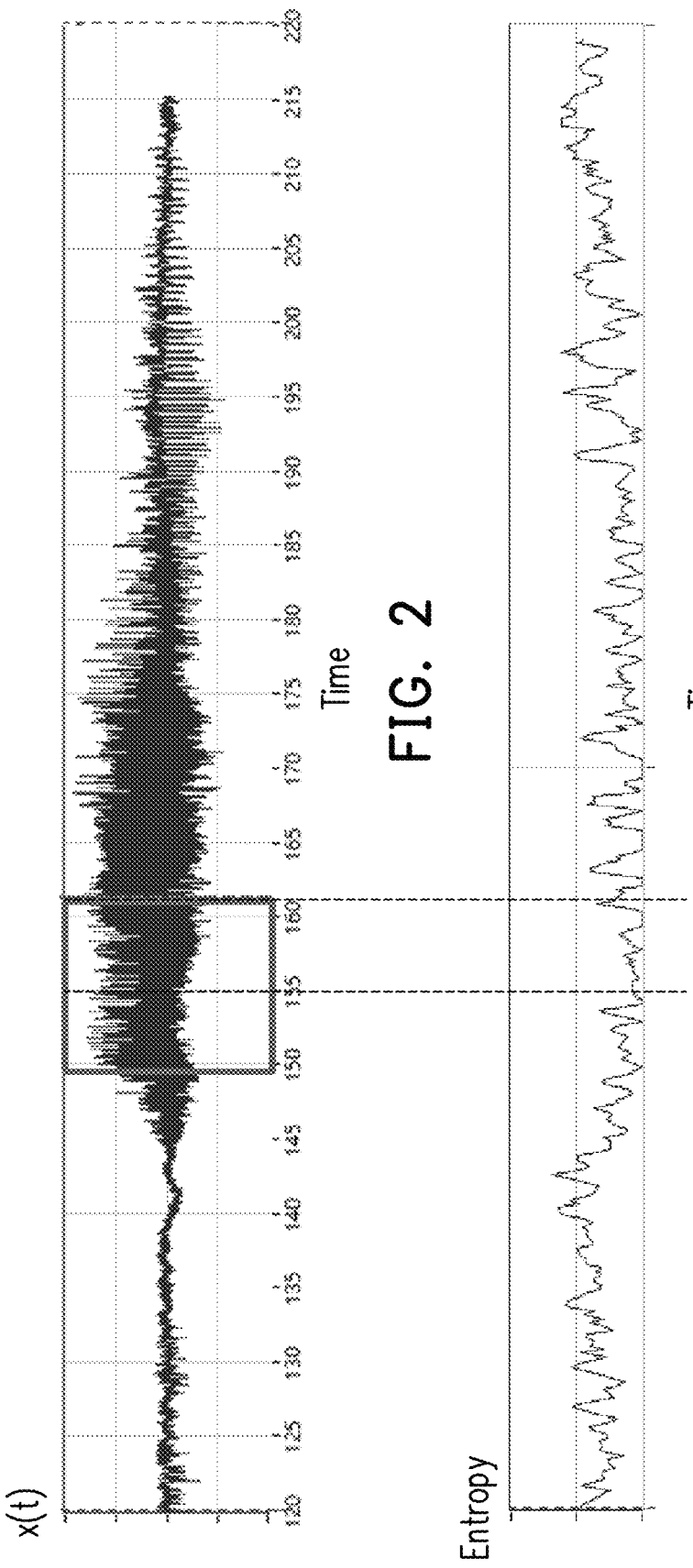
FIG. 2 illustrates a waveform of an ictal neural signal according to an embodiment of the invention.
FIG. 3 illustrates an entropy of an ictal neural signal according to an embodiment of the invention.

FIG. 2 illustrates a waveform of an ictal neural signal, and FIGS. 3 to 6 illustrates the entropy, the line length, the energy density, the energy of entropy of the ictal neural signal respectively, according to an embodiment of the invention.

Figure 4:
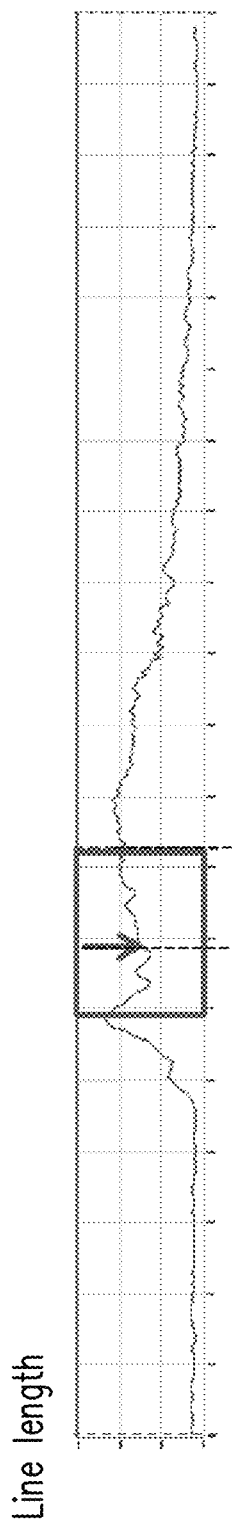
FIG. 4 illustrates a line length of an ictal neural signal according to an embodiment of the invention.
Figure 5:
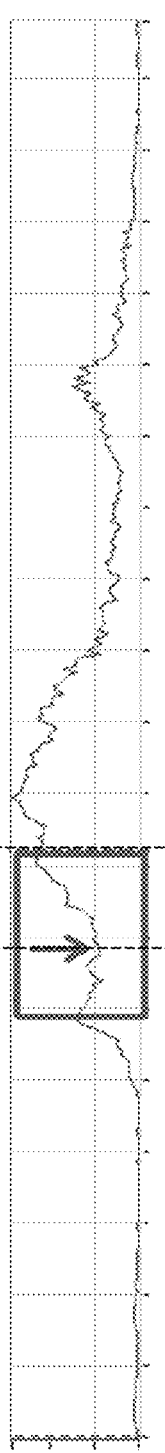
FIG. 5 illustrates an energy density of an ictal neural signal according to an embodiment of the invention.
Figure 6:
FIG. 6 illustrates an energy of entropy of an ictal neural signal according to an embodiment of the invention.

In the embodiment, the controller 120 acquires the ictal neural signal ES from the detector 20 through the receiving circuit 110, where the waveform of the ictal neural signal ES is illustrated by function x(t) in FIG. 2. According to the waveform of the ictal neural signal ES, the controller 120 can calculate characteristics of the ictal neural signal ES such as the entropy as illustrated in FIG. 3, the line length as illustrated in FIG. 4, the energy density as illustrated in FIG. 5, and the energy of entropy as illustrated in FIG. 6. One skilled in the art should have the abilities to find the way for obtaining said characteristics from the waveform of the ictal neural signal ES, therefore details of the calculations are not described herein.

In the embodiment, the controller 120 determines a time point (e.g., in the irregular phase) for starting the electrical stimulation based on the waveform of the ictal neural signal ES. More specifically, the controller 120 first finds a first time point t1 that the line length and energy density are both decreasing, then finds a second time point t2 that the energy of entropy is increasing. The second time point t2 found is likely being in the irregular phase, therefore the controller 120 may determine the second time point t2 as the time point to start the electrical stimulation, and generate and transmit a control signal CS to the stimulator 300 at the second time point t2 for triggering the electrical stimulation.

From another aspect, the controller 120 in the embodiment identifies the pre-ictal phase (ends at the time second time point t2, for example) and the irregular phase (starts from the time second time point t2, for example) in the ictal neural signal ES, and determines the time point to start the electrical stimulation in the irregular phase.

In some embodiments after the electrical stimulation controlling device 100 is notified that the seizure onset has been occurring, it determines how to provide the electrical stimulation. Specifically, the electrical stimulation controlling device 100 determines the stimulation waveform of the electrical stimulation provided to the subject according the ictal neural signal ES. For example, the stimulation waveform can vary with different ictal states determined based on the ictal neural signal ES. In some embodiments, the ictal states can correspond to different waveforms of the irregular phases as such the stimulation waveform is determined by the waveform of the irregular phase identified in the ictal neural signal ES. In some embodiments, the ictal states can correspond to the number of times that the electrical stimulation has been provided before.

More specifically, in some embodiments, the electrical stimulation controlling device 100 includes at least a receiving circuit 110, a controller 120 and a memory 130, where the receiving circuit 110 and the controller 120 are similar as which aforementioned. The memory 130 is coupled to the controller 120 and configured to store plurality of waveforms corresponding to a plurality of ictal states as shown in Table 1 below. Once the receiving circuit 110 receives the onset signal OS, the controller 120 determines the seizure onset accordingly and acquires the ictal neural signal ES through the receiving circuit 110. Afterwards, the controller 120 may determine the ictal state according to the ictal neural signal ES, access the memory 130 in order to find the waveform corresponding to the ictal state determined and determine it as the stimulation waveform.

TABLE 1

| Ictal state | Waveform |
|---|---|
| IS1 | WV1 |
| IS2 | WV2 |
| ... | ... |

Figure 7:
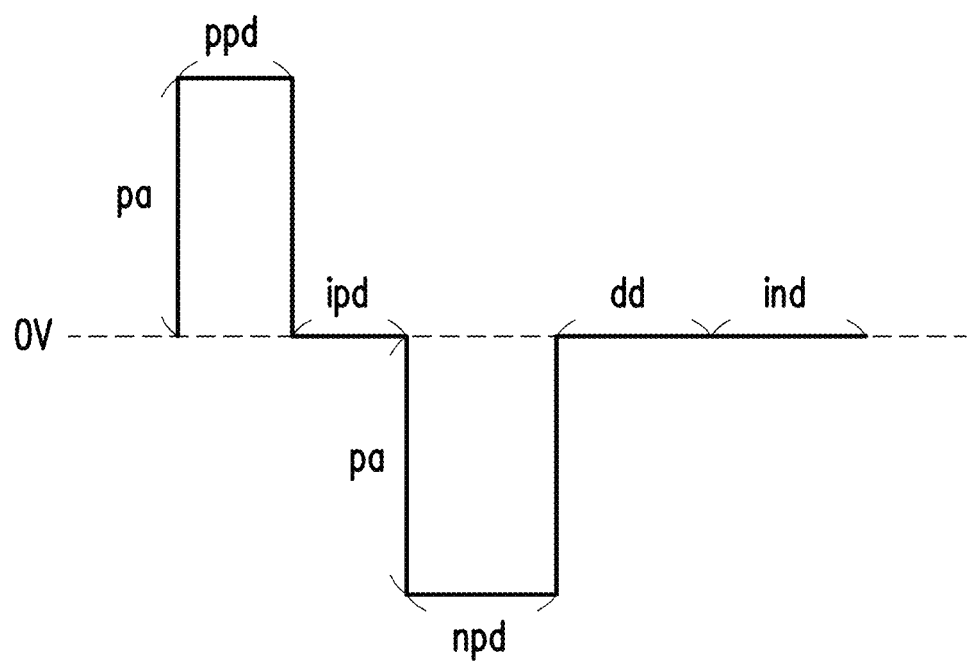
FIG. 7 illustrates a schematic diagram of a waveform according to an embodiment of the invention.

FIG. 7 illustrates a schematic diagram of a waveform according to an embodiment of the invention.

In some embodiments, each of the waveforms (e.g., waveform WV1, waveform WV2, etc.) in the memory 130 can be stored by using multiple parameters, such as a combination of one or more of a pulse amplitude, positive pulse duration, a negative pulse duration, a discharge duration, an inter-phase duration, an in-active duration. Referring to FIG. 7, the parameters includes at least the pulse amplitude pa, the positive pulse duration ppd, the interphase duration ipd, the negative pulse duration npd, the discharge duration dd, and the in-active duration ind. By using said parameter, the waveform of (the voltage of) the electrical stimulation can be determined. However, how the waveform being stored in the memory 130 is not limited herein. One skilled in the art can make modifications and variations as their needs.

In some embodiments, the ictal states can correspond to different waveforms of the irregular phases. For example, when the ictal neural signal ES shows the irregular phase of a first waveform, the controller 120 may determine that the ictal neural signal ES now corresponds to the ictal state IS1. In this case, the controller 120 may access the memory 130 in order to find the waveform WV1 corresponding to the determined ictal state IS1, and generate and transmit a control signal CS according to the waveform WV1 for providing the electrical stimulation in the waveform WV1. Similarly, when the ictal neural signal ES shows the irregular phase of a second waveform, the controller 120 may determine that the ictal neural signal ES now corresponds to the ictal state IS2. In this case, the controller 120 may access the memory 130 in order to find the waveform WV2 corresponding to the determined ictal state IS2, and generate and transmit a control signal CS according to the waveform WV2 for providing the electrical stimulation in the waveform WV2.

In some embodiments, the ictal states can correspond to the number of times that the electrical stimulation has been provided before. Specifically, if an electrical stimulation (also referred as to "the first electrical stimulation") controls the seizure well, the controller 120 is not supposed to trigger an electrical stimulation again (also referred as to "the second electrical stimulation") after an electrical stimulation is provided since, for example, the irregular phase disappears in the ictal neural signal ES. In contrast, if the controller 120 triggers the second electrical stimulation after the electrical stimulation is provided, which means that the seizure is not well-controlled by the first electrical stimulation. Therefore, the second electrical stimulation can be different from (e.g., stronger than) the first electrical stimulation. For example, the controller 120 may determine that the ictal neural signal ES now corresponds to the ictal state IS1 if no electrical stimulation has been provided before, and to the ictal state IS2 if one electrical stimulation has been provided before. In this case, the pulse amplitude pa of the waveform WV2 can be greater than the pulse amplitude pa of the waveform WV1, for example.

One skilled in the art can define the ictal states of an ictal neural signal ES as their needs, such that the controller 120 can determine the stimulation waveform of the electrical stimulation according to the ictal neural signal ES.

In light of the foregoing, the electrical stimulation controlling device and the electrical stimulation system provided by the embodiments of the invention first determine the onset of the neural event according to the neural signal, then analyze the ictal neural signal and determine when and/or how to provide the electrical stimulation. In some embodiment that the neural event is a seizure, the electrical stimulation controlling device and the electrical stimulation system identify multiple ictal phases in the ictal neural signal and select the irregular phase to start the electrical stimulation. Accordingly, the electrical stimulation can be provided accurately and efficiently. In addition to power saving, the increase of endurance of patient due to prolonged electrical stimulations can be avoided.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An electrical stimulation controlling device, comprising:
   a receiving circuit, configured to receive an ictal neural signal which is a signal obtained by a detector when a neural event has been occurring; and
   a controller, coupled to the receiving circuit and a stimulator, and configured to:
      determine a time point to start an electrical stimulation according to the ictal neural signal after an onset of the neural event has been determined; and
      generate and transmit a control signal to the stimulator for providing the electrical stimulation according to the determined time point,
      wherein when determining the time point to start the electrical stimulation according to the ictal neural signal, the controller is configured to:
         identify a plurality of ictal phases in the ictal neural signal for determining the time point,
         wherein when identifying the ictal phases in the ictal neural signal for determining the time point, the controller is configured to:
            continuously calculate a line length, an energy density and an energy of entropy of the ictal neural signal;
            determine a first time point that the line length and the energy density are decreasing; and
            determine a second time point that the energy of entropy increases after the first time point, as the time point to start the electrical stimulation.

2. The electrical stimulation controlling device as claimed in claim 1, wherein before determining the time point to start the electrical stimulation according to the ictal neural signal, the controller is further configured to determine the onset of the neural event.

3. The electrical stimulation controlling device as claimed in claim 1, wherein the receiving circuit is further configured to receive an onset signal indicating the onset of the neural event from an external circuit, and to acquire the ictal neural signal in response to the onset signal received, wherein the onset of the neural event is determined by the controller according to the onset signal.

4. The electrical stimulation controlling device as claimed in claim 1, wherein when generating the control signal at the determined time point, the controller is further configured to:
   determine a stimulation waveform of an electrical stimulation signal according to the ictal neural signal.

5. The electrical stimulation controlling device as claimed in claim 4, further comprising:
   a memory, coupled to the controller and configured to store a plurality of waveforms corresponding to a plurality of ictal states,
   wherein the controller is configured to:
      determine one of the ictal states according to the ictal neural signal;
      determine one of the waveforms corresponding to the determined ictal state stored in the memory, as the stimulation waveform; and
      generate the control signal according to the determined stimulation waveform.

6. The electrical stimulation controlling device as claimed in claim 1, wherein the neural event is a seizure and the determined time point is in an irregular phase within the ictal phases.

7. An electrical stimulation system, comprising:
   an event determination device coupled to a detector;
   an electrical stimulation controlling device coupled to the detector and the event determination device; and
   a stimulator coupled to the electrical stimulation controlling device,
   wherein the event determination device is configured to:
      receive a neural signal from the detector;
      detect an onset of a neural event according to the neural signal; and
      generate and transmit an onset signal to the electrical stimulation controlling device in response to the onset of the neural event detected,
   wherein the electrical stimulation controlling device is configured to:
      receive the onset signal from the event determination device;
      acquire an ictal neural signal from the detector in response to the onset signal received;
      determine a time point to start an electrical stimulation according to the acquired ictal neural signal; and
      generate and transmit a control signal to the stimulator according to the determined time point, wherein the stimulator is configured to receive the control signal and provide the electrical stimulation according to the received control signal,
   wherein when determining the time point to start the electrical stimulation according to the ictal neural signal, the electrical stimulation controlling device is configured to:
      identify a plurality of ictal phases in the ictal neural signal for determining the time point,
      wherein when identifying the ictal phases in the ictal neural signal for determining the time point, the electrical stimulation controlling device is configured to:
         continuously calculate a line length, an energy density and an energy of entropy of the ictal neural signal;
         determine a first time point that the line length and the energy density are decreasing; and
         determine a second time point that the energy of entropy increases after the first time point, as the time point to start the electrical stimulation.

8. The electrical stimulation system as claimed in claim 7, wherein when generating the control signal at the determined time point, the electrical stimulation controlling device is further configured to:
   determine a stimulation waveform of an electrical stimulation signal according to the ictal neural signal.

9. The electrical stimulation system as claimed in claim 8, further comprising:
   a memory, coupled to the electrical stimulation controlling device and configured to store a plurality of waveforms corresponding to a plurality of ictal states,
   wherein the electrical stimulation controlling device is configured to:
      determine one of the ictal states according to the ictal neural signal;
      determine one of the waveforms corresponding to the determined ictal state stored in the memory, as the stimulation waveform; and
      generate the control signal according to the determined stimulation waveform.

10. The electrical stimulation system as claimed in claim 7, wherein the neural event is a seizure and the determined time point is in an irregular phase within the ictal phases.

11. An electrical stimulation controlling device, comprising:
    a receiving circuit, configured to acquire an ictal neural signal which is a signal obtained by a detector when a neural event has been occurring; and
    a controller, coupled to the receiving circuit and a stimulator, and configured to:
       identify a plurality of ictal phases in the ictal neural signal;
       generate a control signal according to the identified ictal phases; and
       transmit the control signal to the stimulator for providing an electrical stimulation,
    wherein when generating the control signal according to the identified ictal phases, the controller is configured to:
       determine a time point to start an electrical stimulation in a concerned ictal phase of the identified ictal phases; and
       generate the control signal according to the determined time point,
    wherein when determining the time point to start the electrical stimulation in the concerned ictal phase of the identified ictal phases, the controller is configured to:
       continuously calculate a line length, an energy density and an energy of entropy of the ictal neural signal;
       determine a first time point that the line length and the energy density are decreasing; and
       determine a second time point that the energy of entropy increases after the first time point, as the time point to start the electrical stimulation.

12. The electrical stimulation controlling device as claimed in claim 11, wherein the neural event is a seizure and the concerned ictal phase is an irregular phase.

13. The electrical stimulation controlling device as claimed in claim 11, wherein when generating the control signal according to the identified ictal phases, the controller is configured to:

determine a stimulation waveform of an electrical stimulation signal according to the ictal neural signal.

14. The electrical stimulation controlling device as claimed in claim 13, further comprising:
a memory, coupled to the controller and configured to store a plurality of waveforms corresponding to a plurality of ictal states,
wherein the controller is configured to:
determine one of the ictal states according to the ictal neural signal;
determine one of the waveforms corresponding to the determined ictal state stored in the memory, as the stimulation waveform; and
generate the control signal according to the determined stimulation waveform.

* * * * *